United States Patent [19]

Sobol et al.

[11] Patent Number: 5,674,486
[45] Date of Patent: Oct. 7, 1997

[54] CANCER IMMUNOTHERAPY WITH CARRIER CELLS

[75] Inventors: Robert E. Sobol; Fred H. Gage; Ivor Royston; Theodore Friedmann, all of La Jolla, Calif.

[73] Assignee: San Diego Regional Cancer Center, San Diego, Calif.

[21] Appl. No.: 473,123

[22] Filed: Jun. 6, 1995

Related U.S. Application Data

[63] Continuation of Ser. No. 68,989, May 27, 1993, abandoned, which is a continuation of Ser. No. 911,346, Jul. 8, 1992, abandoned, which is a continuation of Ser. No. 720,872, Jun. 25, 1991, abandoned.

[51] Int. Cl.$^6$ .......................... A61K 48/00; A61K 35/76; C12N 5/00
[52] U.S. Cl. .................. 424/93.21; 435/375; 435/320.1; 435/69.1; 435/172.3; 435/69.52; 935/62; 935/71; 935/33; 424/93.21; 424/277.1
[58] Field of Search .................. 435/320.1, 240.2, 435/6, 172.3, 69.5, 7.2, 240.21, 375; 514/44; 935/62, 52, 55, 56, 57, 34, 70, 71, 33, 65; 424/93.1, 93.2, 277.1

[56] References Cited

U.S. PATENT DOCUMENTS 5,100,664  3/1992  Doyle et al. ........................ 424/92

OTHER PUBLICATIONS

Blankenstein et al. Eur. J. Immunol. 20:2699–2705, 1990.

Bystryn et al, Cancer & Metastatic Veviews 9: 81–91, 1990.

Colombo et al. Immunology Today 12(7):249–250, 1991.

Harevveni et al, Proc Natl Acad Sci, USA 87:9498–9502, 1990.

Butler et al, Immunopharmacology & Immunotoxicity 11(2&3) 445–487, 1989.

Lanzavecchia A. Science 260:937–944, 1993.

*Primary Examiner*—Jasemine C. Chambers
*Assistant Examiner*—Karen M. Hauda
*Attorney, Agent, or Firm*—Campbell & Flores LLP

[57] ABSTRACT

A novel method of tumor immunotherapy is described comprising the genetic modification of cells resulting in the secretion of cytokine gene products to stimulate a patient's immune response to tumor antigens. In one embodiment, autologous fibroblasts genetically modified to secrete at least one cytokine gene product are utilized to immunize the patient in a formulation with tumor antigens at a site other than an active tumor site. In another embodiment, cells genetically modified to express at least one tumor antigen gene product and to secrete at least one cytokine gene product are utilized in a formulation to immunize the patient at a site other than an active tumor site.

43 Claims, No Drawings

CANCER IMMUNOTHERAPY WITH CARRIER CELLS

This application is a continuation of application Ser. No. 08/068,989, filed May 27, 1993, now abandoned, which is a continuation of application Ser. No. 07/911,346, filed Jul. 8, 1992, now abandoned, which is a continuation of application Ser. No. 07/720,872, filed Jun. 25, 1991, now abandoned.

BACKGROUND

Recent advances in our understanding of the biology of the immune system have lead to the identification of important modulators of immune responses, called cytokines (1–3). Immune system modulators produced by lymphocytes are termed lymphokines, a subset of the cytokines. These agents mediate many of the immune responses involved in anti-tumor immunity. Several of these cytokines have been produced by recombinant DNA methodology and evaluated for their anti-tumor effects. The administration of lymphokines and related immunomodulators has resulted in objective tumor responses in patients with various types of neoplasms (4–7). However, current modes of cytokine administration are frequently associated with toxicities that limit the therapeutic value of these agents.

For example, interleukin-2 (IL-2) is an important lymphokine in the generation of anti-tumor immunity (4). In response to tumor antigens, a subset of lymphocytes termed helper T-cells secrete small quantities of IL-2. This IL-2 acts locally at the site of tumor antigen stimulation to activate cytotoxic T-cells and natural killer cells which mediate systemic tumor cell destruction. Intravenous, intralymphatic and intralesional administration of IL-2 has resulted in clinically significant responses in some cancer patients (4–6). However, severe toxicities (hypotension and edema) limit the dose and efficacy of intravenous and intralymphatic IL-2 administration (5–7). The toxicity of systemically administered lymphokines is not surprising as these agents mediate local cellular interactions and they are normally secreted in only very small quantities.

Additionally, other cytokines, such as interleukin-4 (IL-4), alpha interferon ($\alpha$-INF) and gamma interferon ($\gamma$-INF) have been used to stimulate immune responses to tumor cells. Like IL-2, the current modes of administration have adverse side effects.

To circumvent the toxicity of systemic cytokine administration, several investigators have examined intralesional injection of IL-2. This approach eliminates the toxicity associated with systemic IL-2 administration (8,9,10). However, multiple intralesional injections are required to optimize therapeutic efficacy (9,10). Hence, these injections are impractical for many patients, particularly when tumor sites are not accessible for injection without potential morbidity.

An alternative approach, involving cytokine gene transfer into tumor cells, has resulted in significant anti-tumor immune responses in several animal tumor models (11–14). In these studies, the expression of cytokine gene products following cytokine gene transfer into tumor cells has abrogated the tumorigenicity of the cytokine-secreting tumor cells when implanted into syngeneic hosts. The transfer of genes for IL-2 (11,12), $\gamma$-INF (13) or interleukin-4 (IL-4) (14) significantly reduced or eliminated the growth of several different histological types of murine tumors. In the studies employing IL-2 gene transfer, the treated animals also developed systemic anti-tumor immunity and were protected against subsequent tumor challenges with the unmodified parental tumor (11,12). Similar inhibition of tumor growth and protective immunity was also demonstrated when immunizations were performed with a mixture of unmodified parental tumor cells and genetically modified tumor cells engineered to express the IL-2 gene. No toxicity associated with localized lymphokine transgene expression was reported in these animal tumor studies (11–14).

While the above gene-transfer procedure has been shown to provide anti-tumor immunity, it still retains practical difficulties. This approach is limited by the inability to transfer functional cytokine genes into many patients' tumor cells, as most patients' tumors cannot be established to grow in vitro and methods for human in vivo gene transfer are not available.

SUMMARY OF THE INVENTION

The present invention demonstrates a novel, more practical method of cytokine cancer immunotherapy. In one approach, selected cells from a patient, such as fibroblasts, obtained, for example, from a routine skin biopsy, are genetically modified to express one or more cytokines. Alternatively, patient cells which may normally serve as antigen presenting cells in the immune system such as macrophages, monocytes, and lymphocytes may also be genetically modified to express one or more cytokines. These modified cells are hereafter called cytokine-expressing cells, or CE cells. The CE cells are then mixed with the patient's tumor antigens, for example in the form of irradiated tumor cells, or alternatively in the form of purified natural or recombinant tumor antigen, and employed in immunizations, for example subcutaneously, to induce systemic anti-tumor immunity.

The cytokines are locally expressed at levels sufficient to induce or augment systemic anti-tumor immune responses via local immunization at sites other than active tumor sites. Systemic toxicity related to cytokine administration should not occur because the levels of cytokine secreted by the CE cells should not significantly affect systemic cytokine concentrations.

As the amount of cytokine secreted by the CE cells is sufficient to induce anti-tumor immunity but is too low to produce substantial systemic toxicity, this approach provides the benefit of local cytokine administration. In addition, this novel method obviates the need for intralesional injections, which may produce morbidity. Furthermore, the continuous local expression of cytokine(s) at the sites of immunization may also augment anti-tumor immune responses compared to intermittent cytokine injections. This method also provides the advantage of local immunization with the CE cells, as opposed to cumbersome intravenous infusions. This method also eliminates the need for establishing tumor cell lines in vitro as well as transfer of genes into these tumor cells.

This invention also provides an alternative means of localized expression of cytokines to induce and/or increase immune responses to a patient's tumor through genetic modification of cellular expression of both cytokine(s) and tumor antigen(s). In this embodiment, selected cells from a patient are isolated and transduced with cytokine gene(s) as well as gene(s) coding for tumor antigen(s). The transduced cells are called "carrier cells". Carrier cells can include fibroblasts and cells which may normally serve as antigen presenting cells in the immune system such as macrophages, monocytes, and lymphocytes. Transduced carrier cells actively expressing both the cytokine(s) and the tumor antigen(s) are selected and utilized in local immunizations at a site other than active tumor sites to induce anti-tumor immune responses. As with the CE cells, these carrier cells should not produce substantial systemic toxicities, as the levels of cytokine(s) secreted by the carrier cells should not significantly affect systemic cytokine concentrations. This alternate embodiment is advantageous because it obviates the need to obtain samples of the tumor, which is sometimes difficult. However, carrier cells can be utilized in local immunizations in conjunction with tumor cells, tumor cell homogenates, purified tumor antigens, or recombinant tumor antigens to enhance anti-tumor immunity.

Additionally, this second embodiment retains the same advantages as the first embodiment in that the level of cytokine released by the carrier cells is sufficient to induce anti-tumor immunity but is too low to produce substantial systemic toxicity. In addition, as with the first embodiment, this method obviates the need for intralesional injections, and allows for continuous expression of cytokine(s). This method also eliminates the need for establishing continuous cultures in vitro of tumor cells as well as transfer of genes into these tumor cells, and provides the advantage of local immunization with the carrier cells, as opposed to cumbersome lengthy intravenous infusions.

These approaches may also find application in inducing or augmenting immune responses to other antigens of clinical significance in other areas of medical practice.

DETAILED DESCRIPTION

A novel method of tumor immunotherapy is described comprising the genetic modification of cells resulting in the secretion of cytokine gene products to stimulate a patient's immune response to tumor antigens. "Gene" is defined herein to be a nucleotide sequence encoding the desired protein. In one embodiment, autologous fibroblasts genetically modified to secrete at least one cytokine gene product are utilized to immunize the patient in a formulation with tumor antigens at a site other than an active tumor site. In another embodiment, cells genetically modified to express at least one tumor antigen gene product and to secrete at least one cytokine gene product are utilized in a formulation to immunize the patient at a site other than an active tumor site. Cytokines are preferably expressed in cells which efficiently secrete these proteins into the surrounding milieu. Fibroblasts are an example of such cells. Fibroblasts or other cells can be genetically modified to express and secrete one or more cytokines, as described later in this specification.

Tumor antigens can be provided by several methods, including, but not limited to the following: 1) CE cells can be transduced with gene(s) coding for tumor antigens. These "carrier cells" are then utilized in patient immunizations. 2) Cloned gene sequences coding for appropriate tumor antigens can be transferred into cells such as fibroblasts or antigen-presenting cells. These cells are then mixed with CE or carrier cells to immunize the patient. 3) Tumor antigens can be cloned in bacteria or other types of cells by recombinant procedures. These antigens are then purified and employed in immunizations with CE and/or carrier cells. 4) Tumor antigens can be purified from tumor cells and used, along with CE or carrier cells, to immunize the patient. 5) Tumor cells may be irradiated or mechanically disrupted and mixed with CE and/or carrier cells for patient immunizations.

This invention encompasses the following steps: (A) isolation of appropriate cells for generation of CE cells or carrier cells; (B) isolation of cytokine genes or isolation of cytokine genes and tumor antigen genes, as well as appropriate marker and/or suicide genes; (C) transfer of the genes from (B) to produce the CE cells or carrier cells; (D) preparation of immunological samples of the patient's tumor antigens or other suitable tumor antigens for immunization with CE or carrier cells; (E) inactivation of the malignant potential of tumor cells if they are used as a source of tumor antigens for immunization; and (F) preparation of samples for immunization. Following are several embodiments contemplated by the inventors. However, it is understood that any means known by those in the art to accomplish these steps will be usable in this invention.

(A) Isolation of Cells to Generate CE and Carrier Cells

Cells to be utilized as CE cells and carrier cells can be selected from a variety of locations in the patient's body. For example, skin punch biopsies provide a readily available source of fibroblasts for use in generating CE cells, with a minimal amount of intrusion to the patient. Alternatively, these fibroblasts can be obtained from the tumor sample itself. Cells of hematopoietic origin may be obtained by venipuncture, bone marrow aspiration, lymph node biopsies, or from tumor samples. Other appropriate cells for the generation of CE or carrier cells can be isolated by means known in the art. Non-autologous cells similarly selected and processed can also be used.

(B) Isolation of Genes

Numerous cytokine genes have been cloned and are available for use in this protocol. The genes for IL-2, γ-INF and other cytokines are readily available (1–5, 11–14). Cloned genes of the appropriate tumor antigens are isolated according to means known in the art.

Selectable marker genes such as neomycin resistance ($Neo^R$) are readily available. Incorporation of a selectable marker gene(s) allows for the selection of cells that have successfully received and express the desired genes. Other selectable markers known to those in the art of gene transfer may also be utilized to generate CE cells or carrier cells expressing the desired transgenes.

"Suicide" genes can be incorporated into the CE cells or carrier cells to allow for selective inducible killing after stimulation of the immune response. A gene such as the herpes simplex virus thymidine kinase gene (TK) can be used to create an inducible destruction of the CE cells or carrier cells. When the CE cells or carrier cells are no longer useful, a drug such as acyclovir or gancyclovir can be administered. Either of these drugs will selectively kill cells expressing TK, thus eliminating the implanted transduced cells. Additionally, a suicide gene may be a gene coding for a non-secreted cytotoxic polypeptide attached to an inducible promoter. When destruction of the CE or carrier cells is desired, the appropriate inducer of the promoter is administered so that the suicide gene is induced to produce cytotoxic polypeptide which subsequently kills the CE or carrier cell. However, destruction of the CE or carrier cells may not be required.

Genes coding for tumor antigen(s) of interest can be cloned by recombinant methods. The coding sequence of an antigen expressed by multiple tumors may be utilized for many individual patients.

(C) Transfer of genes

Numerous methods are available for transferring genes into cultured cells (15). For example, the appropriate genes can be inserted into vectors such as plasmids or retroviruses and transferred into the cells. Electroporation, lipofection and a variety of other methods are known in the field and can be implemented.

One method for gene transfer is a method similar to that employed in previous human gene transfer studies, where tumor infiltrating lymphocytes (TILs) were modified by retroviral gene transduction and administered to cancer patients (16). In this Phase I safety study of retroviral mediated gene transfer, TILs were genetically modified to express the Neomycin resistance (Neo$^R$) gene. Following intravenous infusion, polymerase chain reaction analyses consistently found genetically modified cells in the circulation for as long as two months after administration. No infectious retroviruses were identified in these patients and no side effects due to gene transfer were noted in any patients (16). These retroviral vectors have been altered to prevent vital replication by the deletion of viral gag, pol and env genes.

When retroviruses are used for gene transfer, replication competent retroviruses may theoretically develop by recombination between the retroviral vector and vital gene sequences in the packaging cell line utilized to produce the retroviral vector. We will use packaging cell lines in which the production of replication competent virus by recombination has been reduced or eliminated. Hence, all retroviral vector supernatants used to infect patient cells will be screened for replication competent virus by standard assays such as PCR and reverse transcriptase assays (16). Furthermore, exposure to replication competent virus may not be harmful. In studies of subhuman primates injected with a large inoculum of replication competent murine retrovirus, the retrovirus was cleared by the primate immune system (17). No clinical illnesses or sequelae resulting from replication competent virus have been observed three years after exposure. In summary, it is not expected that patients will be exposed to replication competent murine retrovirus and it appears that such exposure may not be deleterious (17).

(D) Preparation of Immunological Samples of the Patient's Tumor Antigens or Purified Recombinant Tumor Antigens Tumor cells bearing tumor associated antigens are isolated from the patient. These cells can derive either from solid tumors or from leukemic tumors. For solid tumors, single-cell suspensions can be made by mechanical separation and washing of biopsy tissue (18).

Hematopoietic tumors may be isolated from peripheral blood or bone marrow by standard methods (19).

A second variant is the use of homogenates of tumor cells. Such homogenates would contain tumor antigens available for recognition by the patient's immune system upon stimulation by this invention. Either unfractionated cell homogenates, made, for example, by mechanical disruption or by freezing and thawing the cells, or fractions of homogenates preferably with concentrated levels of tumor antigens, can be used.

Likewise, purified tumor antigens, obtained for example by immunoprecipitation or recombinant DNA methods, could be used. Purified antigens would then be utilized for immunizations together with the CE cells and/or carrier cells described above to induce or enhance the patient's immune response to these antigens.

In the embodiments employing carrier cells, tumor antigens are available through their expression by the carrier cells. These carrier cells can be injected alone or in conjunction with other tumor antigen preparations or CE cells. Likewise, when CE cells are used, purified recombinant tumor antigen, produced by methods known in the art, can be used.

If autologous tumor cells are not readily available, heterologous tumor cells, their homogenates, their purified antigens, or carrier cells expressing such antigens could be used.

(E) Inactivation of Tumor Cells

When viable tumor cells are utilized in immunizations as a source of tumor antigens, the tumor cells can be inactivated so that they do not grow in the patient. Inactivation can be accomplished by several methods. The cells can be irradiated prior to immunization (18). This irradiation will be at a level which will prevent their replication. Such viable cells can then present their tumor antigens to the patient's immune system, but cannot multiply to create new tumors.

Alternatively, tumor cells that can be cultured may be transduced with a suicide gene. As described above, a gene such as the herpes simplex thymidine kinase (TK) gene can be transferred into tumor cells to induce their destruction by administration of acyclovir or gancyclovir. After immunization, the TK expressing tumor cells can present their tumor antigens, and are capable of proliferation. After a period of time during which the patient's immune response is stimulated, the cells can be selectively killed. This approach might allow longer viability of the tumor cells utilized for immunizations, which may be advantageous in the induction or augmentation of anti-tumor immunity.

(F) Preparation of Samples for Immunization

CE cells and/or carrier cells and tumor cells, and/or homogenates of tumor cells and/or purified tumor antigen (s), are combined for patient immunization. Approximately $10^7$ tumor cells will be required. If homogenates of tumor cells or purified or non-purified fractions of tumor antigens are used, the tumor dose can be adjusted based on the normal number of tumor antigens usually present on $10^7$ intact tumor cells. The tumor preparation should be mixed with numbers of CE or carrier cells sufficient to secrete cytokine levels that induce anti-tumor immunity (11–12) without producing substantial systemic toxicity which would interfere with therapy.

The cytokines should be produced by the CE cells or the carrier cells at levels sufficient to induce or augment immune response but low enough to avoid substantial systemic toxicity. This prevents side effects created by previous methods' administration of greater than physiological levels of the cytokines.

These mixtures, as well as carrier cells that are utilized alone, will be formulated for injection in any manner known in the art acceptable for immunization. Because it is important that at least the CE cells and carrier cells remain viable, the formulations must be compatible with cell survival. Formulations can be injected subcutaneously, intramuscularly, or in any manner acceptable for immunization.

Contaminants in the preparation which may focus the immune response on undesired antigens should be removed prior to the immunizations.

The following example is provided for illustration of one embodiment of the invention and should not be interpreted as limiting the scope of this invention.

EXAMPLE 1

Immunization with Fibroblasts Expressing IL-2 Mixed with Irradiated Tumor Cells

1) Isolation of Autologous Fibroblasts for Use in Generating IL-2 Secreting CE Cells Skin punch biopsies will be obtained from each patient under sterile conditions. The biopsy tissue will be minced and placed in RPMI 1640 media containing 10% fetal calf serum (or similar media) to establish growth of the skin fibroblasts in culture. The cultured fibroblasts will be utilized to generate IL-2 secreting CE cells by retroviral mediated IL-2 gene transfer.

2) Retroviral Vector Preparation and Generation of IL-2 Secreting CE Cells

The cultured skin fibroblasts will then be infected with a retroviral vector containing the IL-2 and Neomycin resistance (Neo$^R$) genes. An N2 vector containing the Neo$^R$ gene will be used, and has been previously utilized by a number of investigators for in vitro and in vivo work, including investigations with human subjects (16). The IL-2 vector will be generated from an N2-derived vector, LLRNL, developed and described by Friedmann and his colleagues (20). It will be made by replacement of the luciferase gene of LLRNL with a full-length cDNA encoding human IL-2. Retroviral vector free of contaminating replication-competent virus is produced by transfection of vector plasmid constructions into the helper-free packaging cell line PA317. Before infection of patients' cells, the vector will have been shown to be free of helper virus. In the event that helper virus is detected, the vector will be produced in the GP+envAM12 packaging cell line in which the viral gag and pol genes are separated from the env, further reducing the likelihood of helper virus production.

3) Transduction Protocol

The cultured primary fibroblasts will be incubated with supernatant from the packaging cell line as described (20). Supernatant from these cells will be tested for adventitious agents and replication competent virus as described (16) and outlined in Table 1. The fibroblasts are washed and then grown in culture media containing G418, (a neomycin analoque) to select for transduced cells expressing the Neo$^R$ gene. The G418-resistant cells will be tested for expression of the IL-2 gene by measuring the concentration of IL-2 in the culture supernatant by an enzyme linked immunosorbent assay (ELISA) (12). G418-resistant cells expressing IL-2 will be stored at $-70°$ C. until required for subsequent use in immunizations.

TABLE 1

| Adventitious Agents and Safety Testing | |
|---|---|
| 1. | Sterility |
| 2. | Mycoplasma |
| 3. | General Safety |
| 4. | Viral Testing |
|  | LCM Virus |
|  | Thymic agent |
|  | S+/L− eco |
|  | S+/L− xeno |
|  | S+/L− ampho |
|  | 3T3 amplification |
|  | MRC-5/Vero |

4) Preparation of Irradiated Tumor Cells

Tumors obtained from clinically indicated surgical resections or from superficial lymph node or skin metastases will be minced into 2–3 mm pieces and treated with collagenase and DNAse to facilitate separation of the tumor into a single cell suspension. The collected cells will be centrifuged and washed in RPMI 1640 media and then cryopreserved in a solution containing 10% dimethyl sulphoxide and 50% fetal calf serum in RPMI 1640 media. The cells will be stored in liquid nitrogen until the time of administration. Prior to their use in subcutaneous immunizations, the cells will be thawed, washed in media free of immunogenic contaminants, and irradiated with 4,000 rads per minute for a total of 20,000 rads in a cesium irradiator.

5) Patient Selection

Patients will have a histologically confirmed diagnosis of cancer. Patients with tumors that must be resected for therapeutic purposes or with tumors readily accessible for biopsy are most appropriate for this embodiment of the invention.

6) Pretreatment Evaluation

The following pretreatment evaluations will be performed:

1) History and physical examination including a description and quantification of disease activity.

2) Performance Status Assessment

0=Normal, no symptoms

1=Restricted, but ambulatory

2=Up greater than 50% of waking hours, capable of self-care

3=Greater than 50% of waking hours confined to bed or chair, limited self-care

4=Bedridden

3) Pretreatment Laboratory:

CBC with differential, platelet count, PT, PTT, glucose, BUN, creatinine, electrolytes, SGOT, SGPT, LDH, alkaline phosphatase, bilirubin, uric acid, calcium, total protein albumin.

4) Other Analyses:

Urinalysis $CH_{50}$, $C_3$ and $C_4$ serum complement levels

Immunophenotyping of peripheral blood B cell and T cell subsets

Assays for detectable replication-competent virus in peripheral blood cells

PCR assays of peripheral blood leukocytes for Neo$^R$, IL-2 and viral env

5) Other Pretreatment Evaluation:

Chest X-ray and other diagnostic studies including computerized tomography (CT), magnetic resonance imaging (MRI) or radionuclide scans may be performed to document and quantify the extent of disease activity.

Follow-up evaluations of these assessments at regular intervals during the course of therapy (approximately every 1 to 3 months) will be useful in determining response to therapy and potential toxicity, permitting adjustments in the number of immunizations administered.

7) Restrictions on Concurrent Therapy

For optimal effects of this treatment, patients should receive no concurrent therapy which is known to suppress the immune system.

8) Final Formulation

Each patient will receive subcutaneous immunizations with a mixture of irradiated tumor cells and autologous fibroblast CE cells genetically modified to secrete IL-2. Approximately $10^7$ tumor cells will be mixed with $10^7$ fibroblasts known to secrete at least 20 units/ml of IL-2 in tissue culture when semi-confluent (12). The irradiated tumor cells and genetically modified fibroblasts will be placed in a final volume of 0.2 ml normal saline for immunization.

9) Dose Adjustments

At least two subcutaneous immunizations will be administered, two weeks apart, with irradiated tumor cells and autologous fibroblasts genetically modified to secrete IL-2. If no toxicity is observed, subsequent booster immunizations may be administered periodically (at least one week apart) to optimize the anti-tumor immune response.

J) Treatment of Potential Toxicity

Toxic side effects are not expected to result from these immunizations. However, potential side effects of these immunizations are treatable in the following manner:

If massive tumor cell lysis results, any resulting uric acid nephropathy, adult respiratory distress syndrome, disseminated intravascular coagulation or hyperkalemia will be treated using standard methods.

Local toxicity at the sites of immunization will be treated with either topical steroids and/or surgical excision of the injection site as deemed appropriate.

Hypersensitivity reactions such as chills, fever and/or rash will be treated symptomatically with antipyretics and antihistamines. Patients should not be treated prophylactically. Should arthralgias, lymphadenopathy or renal dysfunction occur, treatment with corticosteroids and/or antihistamines will be instituted. Anaphylaxis will be treated by standard means such as administration of epinephrine, fluids, and steroids.

As will be apparent to those skilled in the art to which the invention pertains, the present invention may be embodied in other forms other than those specifically disclosed above without departing from the spirit or essential characteristics of the invention. The particular embodiments of the invention described above, are, therefore to be considered as illustrative and not restrictive. The scope of the present invention is as set forth in the appended claims.

References

1. Gabrilove, J. L. et al., Monogr. J. Natl. Cancer Inst. 10:73–7 (1990).
2. Kelso, A., Current Opinion in Immunology, 2:215–25 (1989).
3. Borden, E. C. et al., Cancer, 65:800–14 (1990).
4. Rosenberg, S. A. et al., Ann. Intern. Med., 108:853–864 (1988).
5. Lotze, M. T. et al., JAMA, 256:3117–3124 (1986).
6. Pizza, G. et al., Lymphokine Research, 7:45–8 (1988).
7. Sarna, G. et al., Journal of Biological Response Modifiers, 9:81–6 (1990).
8. Gandolfi, L. et al., Hepato-Gastroenterology, 36:352–6 (1989).
9. Bubenik, J. et al., Immunol. Letters, 19:279–82 (1988).
10. Bubenik et al., Immunol. Letters, 23:287–292 (1990).
11. Fearon, E. R. et al., Cell, 60:387–403 (1990).
12. Gansbacher, B. et al., J. Exp. Med., 172:1217–1224 (1990).
13. Watanabe, Y. et al., Proc. Natl. Acad. Sci., 86:9456–9460 (1989).
14. Tepper, R. I. et al., Cell, 57:503–512 (1989).
15. Kriegler, M., Gene Transfer and Expression: A Laboratory Manual, Stockton Press (1990).
16. Rosenberg, S. A. et al., N. Eng. J. Med., 370 (1990).
17. Cornetta, K. et al., Prog. Nucl. Acid Res. Mol. Biol., 36:311–22 (1989).
18. Hoover, H. C. et al., Cancer Res., 44:1671–76 (1984).
19. Sobol et al. New Eng. J. Med. 316:1111–1117 (1987).
20. Li Xu, et al., Virology, 171:331–341 (1989).

We claim:

1. A method of stimulating an immune response against a tumor antigen in a patient comprising immunizing said patient at a site other than an active tumor site with a formulation containing carrier cells, wherein said carrier cells express at least one tumor antigen and express and secrete at least one cytokine as a result of exogenously introduced genes coding for said tumor antigen and said cytokine, wherein the expression of said tumor antigen and the expression and secretion of said cytokine result in the stimulation of an immune response specific for said tumor antigen.

2. The method of claim 1 wherein the cytokine gene is selected from the group consisting of interleukin-1, interleukin-2, interleukin-3, interleukin-4, interleukin-5, interleukin-6, and gamma-interferon.

3. The method of claim 2 wherein one cytokine gene is interleukin-1.

4. The method of claim 2 wherein one cytokine gene is interleukin-2.

5. The method of claim 2 wherein one cytokine gene is interleukin-3.

6. The method of claim 2 wherein one cytokine gene is interleukin-4.

7. The method of claim 2 wherein one cytokine gene is interleukin-5.

8. The method of claim 2 wherein one cytokine gene is interleukin-6.

9. The method of claim 2 wherein one cytokine gene is gamma-interferon.

10. The method of claim 1 wherein at least one cytokine gene is transferred into the carrier cells by recombinant methods.

11. The method of claim 10 wherein the recombinant methods are selected from infection, transfection, electroporation and lipofection.

12. The method of claim 10 wherein the cytokine gene is present in an expression vector.

13. The method of claim 12 wherein said expression vector is a retrovirus.

14. The method of claim 12 wherein said expression vector additionally contains a selectable marker gene.

15. The method of claim 14 wherein the selectable marker gene is the gene coding for neomycin resistance.

16. The method of claim 12 wherein said expression vector additionally contains a suicide gene coding for herpes simplex thymidine kinase.

17. The method of claim 16 wherein the suicide function of said suicide gene is activated after stimulation of the patient's immune system.

18. The method of claim 2 wherein each cytokine gene is expressed at a level sufficient to stimulate the immune response but low enough to avoid substantial systemic toxicities.

19. The method of claim 1 wherein the carrier cells are generated from fibroblasts and antigen-presenting cells.

20. The method of claim 19 wherein the antigen-presenting cells are selected from macrophages, monocytes, and antigen presenting lymphocytes.

21. A method for stimulating an immune response against a tumor antigen in a patient, comprising:
   a) isolating fibroblasts from said patient;
   b) culturing said fibroblasts in vitro;
   c) transducing said cultured fibroblasts with a retroviral expression vector containing a gene coding for IL-2 and a gene coding for a tumor antigen, wherein said transduced fibroblasts express said tumor antigen, and express and secrete said IL-2; and
   d) immunizing said patient at a site other than an active tumor site, with said fibroblasts that express said tumor antigen and that express said IL-2 at a level sufficient to enhance an immune response specific for said tumor antigen, but low enough to avoid substantial systemic toxicity, wherein the expression of said tumor antigen and the secretion of said IL-2 result in the stimulation of an immune response specific for said tumor antigen.

22. The method of claim 21 wherein said fibroblasts are further modified to express the Neomycin gene.

23. The method of claim 21, wherein said fibroblasts are further modified to express a suicide gene coding for herpes simplex thymidine kinase.

24. The method of claim 23 wherein the suicide function of said suicide gene is activated after stimulation of the patient's immune system.

25. A composition for stimulating an immune response specific for tumor antigens in a patient, comprising carrier cells genetically modified to express as least one tumor antigen gene and to express and secrete at least one cytokine.

26. The composition of claim 2 wherein the cytokine is selected from the group consisting of interleukin-1, interleukin-2, interleukin-3, interleukin-4, interleukin-5, interleukin-6, and gamma-interferon.

27. The composition of claim 26 wherein one cytokine gene is interleukin-1.

28. The composition of claim 26 wherein one cytokine gene is interleukin-2.

29. The composition of claim 26 wherein one cytokine gene is interleukin-3.

30. The composition of claim 26 wherein one cytokine gene is interleukin-4.

31. The composition of claim 26 wherein one cytokine gene is interleukin-5.

32. The composition of claim 26 wherein one cytokine gene is interleukin-6.

33. The composition of claim 26 wherein one cytokine gene is gamma-interferon.

34. The composition of claim 25 wherein at least one cytokine gene is transferred into the carrier cells by recombinant methods.

35. The composition of claim 34 wherein the recombinant methods are selected from infection, transfection, electroporation and lipofection.

36. The composition of claim 34 wherein the cytokine gene is present in an expression vector.

37. The composition of claim 36 wherein said expression vector is a retrovirus.

38. The composition of claim 36 wherein said expression vector additionally contains a selectable marker gene.

39. The composition of claim 38 wherein the selectable marker gene is the gene coding for neomycin resistance.

40. The composition of claim 36 wherein said expression vector additionally contains a suicide gene coding for herpes simplex thymidine kinase.

41. The composition of claim 40 wherein the suicide function of said suicide gene is activated after stimulation of the patient's immune system.

42. The composition of claim 25 wherein the carrier cells are generated from fibroblasts and antigen-presenting cells.

43. The composition of claim 42 wherein the antigen-presenting cells are selected from macrophages, monocytes, and antigen presenting lymphocytes.

* * * * *

UNITED STATES PATENT AND TRADEMARK OFFICE
CERTIFICATE OF CORRECTION

PATENT NO. : 5,674,486
DATED : October 7, 1997
INVENTOR(S) : Sobol et al.

It is certified that error appears in the above-identified patent and that said Letters Patent is hereby corrected as shown below:

Column 5,
Line 16, please delete "vital" and replace with -- viral --.

Column 11, claim 26,
Line 13, please delete "2" and replace with -- 25 --.

Signed and Sealed this

Nineteenth Day of March, 2002

Attest:

JAMES E. ROGAN
Director of the United States Patent and Trademark Office

Attesting Officer